(12) United States Patent
Denissen et al.

(10) Patent No.: US 8,592,637 B2
(45) Date of Patent: Nov. 26, 2013

(54) PROCESS FOR PREPARING MONONITRATED ORGANIC COMPOUNDS

(75) Inventors: Leo Denissen, Brasschaat (BE); Eckhard Stroefer, Mannheim (DE); Jan-Dirk Arndt, Mannheim (DE); Torsten Mattke, Freinsheim (DE); Kerstin Heinen, Lorsch (DE); Julia Leschinski, Mannheim (DE)

(73) Assignee: BASF SE, Ludwigshafen (DE)

( * ) Notice: Subject to any disclaimer, the term of this patent is extended or adjusted under 35 U.S.C. 154(b) by 92 days.

(21) Appl. No.: 13/393,251

(22) PCT Filed: Aug. 20, 2010

(86) PCT No.: PCT/EP2010/062176
§ 371 (c)(1),
(2), (4) Date: Feb. 29, 2012

(87) PCT Pub. No.: WO2011/023638
PCT Pub. Date: Mar. 3, 2011

(65) Prior Publication Data
US 2012/0157722 A1    Jun. 21, 2012

(30) Foreign Application Priority Data
Aug. 31, 2009 (EP) .................................... 09169016

(51) Int. Cl.
*C07C 205/00* (2006.01)

(52) U.S. Cl.
USPC ............................ 568/939; 568/937; 568/928

(58) Field of Classification Search
USPC ......................................... 568/939, 937, 928
See application file for complete search history.

(56) References Cited

U.S. PATENT DOCUMENTS 6,506,949 B2 * 1/2003 Gillis et al. .................. 568/939
2011/0306795 A1 12/2011 Mackenroth et al.

FOREIGN PATENT DOCUMENTS

WO  2001 046433  6/2001
WO  2001 064333  9/2001

OTHER PUBLICATIONS

U.S. Appl. No. 13/569,806, filed Aug. 8, 2012, Deckert, et al.
U.S. Appl. No. 13/567,265, filed Aug. 6, 2012, Leschinski, et al.
International Search Report issued on Oct. 29, 2010 in PCT/EP10/062176 filed on Aug. 20, 2010.
U.S. Appl. No. 13/434,135, filed Mar. 29, 2012, Lehr, et al.
U.S. Appl. No. 13/479,961, filed May 24, 2012, Stroefer, et al.

* cited by examiner

*Primary Examiner* — Jafar Parsa
(74) *Attorney, Agent, or Firm* — Oblon, Spivak, McClelland, Maier & Neustadt, L.L.P.

(57) ABSTRACT

The present invention relates to a process for continuously preparing a mononitrated organic compound, especially a process for preparing mononitrobenzene. The invention relates more particularly to an improved continuous adiabatic process for preparing nitrobenzene.

20 Claims, No Drawings

PROCESS FOR PREPARING MONONITRATED ORGANIC COMPOUNDS

The present invention relates to a process for continuously preparing a mononitrated organic compound, especially a process for preparing mononitrobenzene. The invention relates more particularly to an improved continuous adiabatic process for preparing nitrobenzene.

Processes for nitrating aromatics, especially for nitrating benzene, have been known for some time and have been used commercially for many years in order to obtain, for example, mononitrobenzene, which is used particularly in the production of aniline. Typically, the preparation of nitrobenzene comprises the addition of nitric acid and sulfuric acid to benzene. This nitration can be performed within the temperature range from 60 to 70° C. with the heat of reaction being led off, or it can be performed under adiabatic conditions. To perform the reaction, nitric acid and sulfuric acid are mixed, and benzene is metered in, which reacts with the nitric acid to give water and essentially nitrobenzene.

The reaction zone in which benzene and nitric acid are reacted may consist of an arrangement of stirred tanks or a tubular reactor, good mixing being required for the reaction. Preference is therefore given to using a tubular reactor in which a plurality of dispersing elements are arranged distributed over the length of the tubular reactor, which ensure intensive mixing of benzene, nitric acid, sulfuric acid and water. Such a reactor is described, for example, in WO 2001/64333 A2.

The essentially nitric acid-free reaction mixture which is obtained after the reaction is fed to a phase separation apparatus in which two phases form, the first of which is referred to as crude nitrobenzene and consists essentially of nitrobenzene, benzene and an amount of sulfuric acid and water dissolved in the nitrobenzene, and the second, referred to as waste acid, consists essentially of water, sulfuric acid and nitrobenzene dissolved in the sulfuric acid.

Since the acid phase and the benzene phase are immiscible during the reaction, the reaction rates and the space-time yield are limited to a high degree by the mass transfer between the phases, i.e. by the ability to expose large interface areas of each of the phases to one another. When the interface areas are enlarged, the reaction rate between the phases is increased. In customary nitrobenzene production plants, these interface areas are created by converting the reaction participants in one or more mixed vessels, where high shear forces are applied to the liquids.

In the industrial nitration of benzene, in addition to the main nitrobenzene product, numerous by-products are also obtained in the order of magnitude of a few 100s of ppm to a few 1000s of ppm. The by-products which occur can be divided into two groups: polynitrated benzenes and phenolic by-products which are mono- or polynitrated. The polynitrated benzenes which occur are the isomeric dinitrobenzenes: 1,2-dinitrobenzene, 1,3-dinitrobenzene and 1,4-dinitrobenzene. The phenolic by-products formed are the isomeric nitrated phenols: 2-nitrophenol, 3-nitrophenol and 4-nitrophenol. The isomeric dinitrated phenols 2,4-dinitrophenol and 2,6-dinitrophenol are also obtained, as is the trinitrated 2,4,6-trinitrophenol (picric acid). Even though the by-products are obtained only in low concentrations, they lead, owing to their high toxicity and ecotoxicity and to the complexity of their removal, to an increased level of complexity in the product and wastewater processing, and therefore impair the economic viability of the nitrobenzene process to a very high degree.

To reduce the occurrence of the aforementioned by-products, an excess of benzene is typically used, and a reactor with a particular configuration is used in order, in particular, to suppress the formation of polynitrated benzenes. For this purpose, for example, WO 01/46433 A2 proposes using a tubular reactor in which dispersing zones alternate with calming zones. However, one disadvantage of this reactor is a significant separation of the phases (sedimentation) in the calming zones of the reactor, which requires very energy-intensive mixing of the individual reactants in the downstream dispersing zones.

It is an object of the present invention to provide a process for continuously preparing nitrated aromatics, especially for preparing nitrobenzene, which can be performed in a tubular reactor of simple construction, and affords a high final conversion and a small amount of by-products.

This object is achieved by a process for continuously preparing nitrated aromatics by reacting at least one aromatic with a mixture comprising nitric acid, sulfuric acid and water, comprising the steps of (a) feeding the at least one aromatic and the mixture comprising nitric acid, sulfuric acid and water in any sequence into a tubular reactor, said tubular reactor having a plurality of vertical tube bends with a deflection angle in the range from 160° to 200°, which are arranged over the total length of the reactor at a distance which corresponds to 30 to 70 times the diameter of the reactor, and a number of static mixing elements which are arranged such that high backmixing exists in a first part of the tubular reactor and lower backmixing in a second part of the reactor, (b) converting the at least one aromatic and the mixture comprising nitric acid, sulfuric acid and water in the reactor under adiabatic conditions in order to obtain a reaction mixture, and (c) separating the reaction mixture obtained in step (b) after performance of the reaction into an organic phase and an aqueous phase.

It has been found that, surprisingly, with the aid of the process according to the invention, aromatic mononitro compounds, especially nitrobenzene, can be prepared in a high yield with a small proportion of by-products, without any need to use costly and complicated reactors.

Use of the tubular reactor which comprises a plurality of vertical tube bends with a deflection angle in the range from 160° to 200°, preferably with a deflection angle of 180°, which are arranged over the entire length of the reactor at a distance which corresponds to 30 to 70 times, preferably to 60 to 40 times, more preferably to 45 to 55 times, the diameter of the reactor, achieves with very minimal apparatus complexity, and low energy supply, very effective mixing of the reactants used, of the at least one aromatic and of the mixture comprising nitric acid, sulfuric acid and water, as a result of which a high dispersing action and hence a high reaction rate are advantageously achieved at the same time. The term "vertical tube bend" is understood in the context of the invention to mean a tube bend which is aligned vertically with respect to the base and which thus serves to redisperse the biphasic mixture. Advantageously, the biphasic mixture is mixed very effectively while it flows through the vertical tube bend with a minimum level of apparatus complexity.

The arrangement of the tube bends in the tubular reactor depends on the reaction conditions. In one embodiment of the invention, the tubular reactor is divided by the bends into 6 to 18 chambers, more preferably into 10 to 12 chambers. In a further embodiment of the invention, the tube bends are arranged equidistantly over the total length of the tubular reactor.

The tubular reactor in which the process according to the invention is performed further comprises a number of static mixing elements which are arranged such that, in interplay with the tube bends, high backmixing exists in a first part of the tubular reactor and lower backmixing in a second part of the tubular reactor. The length of the first part of the tubular reactor in which high backmixing exists is 20 to 40% of the total length of the tubular reactor, preferably 25 to 35% based on the total length of the tubular reactor; the length of the second part of the tubular reactor in which lower backmixing exists is 60 to 80%, preferably 65 to 75%, based on the total length of the tubular reactor. Depending on the reaction conditions, the static mixing elements are arranged such that the above-defined conditions exist in the corresponding sections. "High backmixing" in the context of the invention means that conditions under which the Bodenstein number assumes a value or values of less than 5 exist in this subregion of the reactor. "Lower backmixing" means that conditions under which the Bodenstein number assumes a value or values greater than 5 exist in this subregion of the reactor. The arrangement of the tube bends and of the static mixing elements can be undertaken by the person skilled in the art on the basis of his technical knowledge such that the corresponding conditions exist in corresponding regions of the reactor.

The static mixing elements present in the tubular reactor are preferably restrictors, especially offset restrictors, beds and plates with suitable orifices. Since the high reaction temperatures and the aggressive feedstocks which occur in the adiabatic process regime make high demands on the material of the plates, a material which is virtually inert under these conditions is used for the plates, more preferably stainless steel or tantalum plates, and coated or ceramic materials.

The plates function as dispersing elements, and have orifices. The orifices may be slats, holes or bores. The orifices are preferably bores, since the manufacture thereof is particularly simple to accomplish. It is, however, also possible to select other orifice forms. In one embodiment of the invention, it has been found to be advantageous to use plates configured as perforated plates. These perforated plates have a multitude of holes which, in one embodiment of the invention, are arranged symmetrically or homogeneously over the area of the plate. In a further embodiment of the invention, the perforated plates have areas in which a smaller number of holes per unit area is provided proceeding from a homogeneous distribution of the holes per unit area.

In a particularly preferred embodiment of the invention, it has been found to be advantageous, in the process according to the invention, to use plates which have both bores and triangular and/or quadrangular and/or pentangular and/or hexangular or segment-like cutouts. These cutouts are preferably distributed homogeneously over part of the area of the plate, while the cutouts are arranged distributed over another part of the area of the plate. The triangular and/or quadrangular and/or pentangular and/or hexangular or segment-like cutouts are, in one embodiment of the invention, only partly punched out, and the cutouts are bent out of the plane of the plate, preferably in flow direction, and function as baffles. The use of such plates brings about particularly advantageous mixing of the reactants used in the process according to the invention.

The reactor used in the process according to the invention is preferably aligned vertically and has a lower end and an upper end. The lower end of the reactor has at least one supply means for admittance of the reactants, of the at least one aromatic and of the mixture comprising nitric acid, sulfuric acid and water, and the upper end has at least one removal means for withdrawing the reaction mixture. In one embodiment of the invention, the reactants are supplied with the aid of at least one pump. In a preferred embodiment, the reactor additionally has supply means for the organic and aqueous phases, which enable supply into the individual chambers present in the reactor.

The reaction participants can be supplied together, but also individually or as mixtures of two or three thereof, simultaneously or successively to the reactor. In one embodiment of the invention, the reaction participants can be introduced in the aforementioned manner via one or more feed(s), such as nozzle(s).

Of minor importance for the success of the reaction is the sequence and composition in which the reaction participants, nitric acid, the aromatic and sulfuric acid and water, are mixed with one another, provided that the resulting reaction mixture has the inventive composition after the overall mixing.

In order to prevent undesired backflow through the internals, especially plates, over the entire reactor, preference is given to using, in the tubular reactor, plates which generate a pressure drop of 0.05 to 3 bar per plate. For adiabatic mononitration of aromatics, particular preference is given to using plates which generate a pressure drop of 0.05 to 1 bar, most preferably of 0.08 to 0.8 bar. The pressure drop per plate is preferably kept to a minimum, since providing a higher pressure drop, for example, requires a pump of higher performance, which in turn leads to higher costs in the overall process.

In one embodiment of the invention, the reactants are fed in through at least one feed, which permits the reactants to be fed into the tubular reactor with high mixing. In one embodiment of the invention, the at least one aromatic can be fed into the tubular reactor via one feed, for example a nozzle, and the mixture comprising nitric acid, sulfuric acid and water via a further feed, for example a nozzle; in a preferred embodiment, the at least one aromatic and the mixture comprising nitric acid, sulfuric acid and water can be fed simultaneously into the tubular reactor through one feed, for example through a nozzle. In a further preferred embodiment, the mixture comprising nitric acid, sulfuric acid and water is fed to the tubular reactor through a plurality of feeds, for example through a plurality of nozzles, which are arranged distributed over the length of the tubular reactor.

The nozzle(s) which is or are used in the process according to the invention in a preferred embodiment of the invention are known to the person skilled in the art in the field of reactor technology. The nozzle is preferably configured such that it is capable of releasing a turbulent flow as a divergent transition layer which produces a divergent pattern (full cone) of droplets, and may or may not impart a rotary motion element to the droplets mentioned. Such flow patterns can be obtained by using nozzles known from spray-drying technology. The nozzle preferably has inner walls or other means which define one or more tangential or helical passages in order to create a radial (helical) exit stream which is superimposed on a linear divergent stream in order to obtain a resulting helical stream, which serves to enhance the dispersion of the droplets formed on exit. The nozzle preferably has an exit cone angle of 70° or less.

The feeds used in the process according to the invention are known to the person skilled in the art in the field of reactor technology. The feed is preferably configured such that it already generates premixing. This can be achieved by the use of different mixing nozzles known to those skilled in the art, but also static mixers or a T-piece.

The linear fluid flow rate through the feed, especially through the nozzle, is typically from 5 to 50 m/s, and average droplet sizes of 10 to 1000 μm are achieved.

The reaction participants are mixed in the feed or in the reactor in the range from 20 to 110° C., preferably in the range from 40 to 100° C., more preferably in the range from 55 to 95° C. Adiabatic reaction conditions are maintained. The end temperature depends on the level of the mixing temperature, on the ratios of the reaction participants and on the conversion; it generally does not exceed 140° C., usually not 130° C.

The aromatic compounds which can be used in the present invention are, for example, benzene, toluene, chlorobenzene, naphthalene and anthraquinone. In a preferred embodiment, the aromatic compound is benzene.

The proportion of nitric acid in the mixture comprising nitric acid, sulfuric acid and water is, based on the sum of nitric acid, sulfuric acid and water, 1 to 8% by weight, preferably 2 to 6% by weight, more preferably 2.5 to 4% by weight. Nitric acid can be used in highly concentrated or in azeotropically boiling form, but preferably in the form of the "weak acid" which is approx. 60 to 65% by weight and is available inexpensively.

The sulfuric acid content in the mixture comprising nitric acid, sulfuric acid and water is, based on the sum of nitric acid, sulfuric acid and water, 58 to 74% by weight, preferably 60 to 70% by weight, more preferably 62 to 68% by weight, most preferably 64 to 67% by weight.

The remainder to 100% by weight is water. This can be used as such as dilution water of the sulfuric acid, as dilution water of the nitric acid or in more than one of the forms mentioned. More preferably, water is present as dilution water both of the sulfuric acid and of the nitric acid.

The molar ratio of the at least one aromatic, especially of the benzene, to $HNO_3$ is generally 0.9 to 1.5. In order to minimize the formation of undesired polynitrated aromatics, especially polynitrated benzene, the molar ratio of the aromatic to nitric acid is preferably 1.0 to 1.5, more preferably 1.03 to 1.3, most preferably 1.05 to 1.2. The reaction of the process according to the invention in the case of preparation of nitrobenzene is, in terms of formula: $C_6H_6 + HNO_3 \rightarrow O_2N-C_6H_6 + H_2O$.

Thus, in a preferred embodiment of the invention, benzene and $HNO_3$ are introduced into the process, and mononitrobenzene and water are discharged, while the $H_2SO_4/H_2O$ mixture described constitutes the reaction medium. Since dilute nitric acids are advantageously used in the industrial implementation, it is necessary also to discharge diluent water of the nitric acid in addition to the water of reaction.

Next, the flow rate of the reaction participants is described. Since an optimal flow rate of the reaction participants depends on various factors, such as the reactor size and the reaction conditions, it is not possible to generalize at this point, but, in the case of a tubular reactor with an internal diameter of 50 to 350 mm, the linear flow rate in the tube is usually 0.20 to 3.00 m/s, preferably 0.5 to 1.5 m/s. The residence time of the reaction participants in the tubular reactor depends on the reaction conditions and the tubular reactor, but is usually 0.5 minute to five minutes, preferably 0.5 minute to 2 minutes. The pressure in the reactor is generally 2 to 5 bar abs. This ensures that benzene is present in liquid form under the existing temperature conditions.

The length and internal diameter of the tubular reactor depend on the process parameters; the length of the tubular reactor is generally 2.5 to 300 m, preferably 25 to 200 m, more preferably 100 to 150 m. The internal diameter of the reactor may likewise vary over wide ranges, and is generally 50 to 350 mm, preferably 100 to 300 mm, more preferably 150 to 280 mm.

In step (c), the reaction mixture leaving the tubular reactor is separated into an organic phase and into an acid phase in a separator. The acid phase removed is reconcentrated by well-known means, for example apparatus, for example a vacuum evaporator, in which case the heat generated by the reaction and the mixing is utilized and used again if required. From the organic phase, the desired aromatic nitro compound can be purified by removing impurities present by employing processes which are usually performed in the nitration of an aromatic compound, such as washing and distillation.

The example which follows illustrates the process according to the invention.

EXAMPLE 1

In a tubular reactor with an internal diameter d=200 mm and a length of L=130 m, benzene is reacted with a mixed acid consisting of 65% $H_2SO_4$, 3% $HNO_3$ and 36% water at a starting temperature of T=90° C. under adiabatic conditions, the molar excess of benzene being 10%. The reactor is equipped with a total of 15 static mixing elements, of which 7 are installed in the first third, 5 in the second third and 3 in the third of the reactor volume. At a residence time of t=1.5 min, a nitroaromatic yield of 97% is achieved. The proportion of phenolic secondary components is between 1000 and 5000 ppm. When the reactor is additionally equipped with 12 tube bends with a radius of 180° distributed homogeneously over the length, the yield is increased to 98%, in which case the proportion of phenolic by-products can be reduced by 10%.

The invention claimed is:

1. A process for continuously preparing a nitrated aromatic, the process comprising:
    (a) feeding an aromatic and a mixture comprising nitric acid, sulfuric acid and water into a tubular reactor, to obtain a first reaction mixture,
    wherein the tubular reactor has a plurality of vertical tube bends having a deflection angle of 160° to 200°, which are arranged over a total length of the tubular reactor at a distance which corresponds to 30 to 70 times a diameter of the tubular reactor, and a number of static mixing elements which are arranged such that a Bodenstein number is less than 5 in a first part of the tubular reactor and a Bodenstein number is greater than 5 in a second part of the tubular reactor,
    (b) converting the first reaction mixture in the tubular reactor under an adiabatic condition to obtain a second reaction mixture, and
    (c) separating the second reaction mixture into an organic phase and an aqueous phase.

2. The process of claim 1, wherein the static mixing elements are selected from a bed, a perforated sheet, a restrictor and a static mixer.

3. The process of claim 1, wherein the mixture comprising nitric acid, sulfuric acid and water is fed to the tubular reactor via a plurality of feeds which are distributed over the total length of the tubular reactor.

4. The process of claim 1, wherein a molar ratio of the aromatic to nitric acid is 1.0 to 1.5.

5. The process of claim 1, wherein the tubular reactor is divided by the tube bends into 6 to 18 chambers.

6. The process of claim 1, wherein the aromatic is at least one selected from benzene, toluene, chlorobenzene, naphthalene and anthraquinone.

7. The process of claim 1, wherein the aromatic is benzene.

8. The process of claim 1, wherein a molar ratio of the aromatic to nitric acid is 1.03 to 1.3.

9. The process of claim 1, wherein a molar ratio of the aromatic to nitric acid is 1.05 to 1.2.

10. The process of claim 1, wherein the deflection angle is 180°.

11. The process of claim 1, wherein the plurality of vertical tube bends are arranged over the total length of the tubular reactor at a distance which corresponds to 45 to 55 times the diameter of the tubular reactor.

12. The process of claim 1, wherein the tubular reactor is divided by the tube bends into 10 to 12 chambers.

13. The process of claim 1, wherein a length of the first part of the tubular reactor is 20 to 40% of the total length of the tubular reactor, and a length of the second part of the tubular reactor is 60 to 80% of the total length of the tubular reactor.

14. The process of claim 1, wherein a length of the first part of the tubular reactor is 25 to 35% of the total length of the tubular reactor, and a length of the second part of the tubular reactor is 65 to 75% of the total length of the tubular reactor.

15. The process of claim 1, wherein the mixture comprising nitric acid, sulfuric acid, and water comprises 1 to 8 wt % nitric acid and 58 to 74 wt % sulfuric acid.

16. The process of claim 1, wherein the mixture comprising nitric acid, sulfuric acid, and water comprises 2.5 to 4 wt % nitric acid and 64 to 67 wt % sulfuric acid.

17. The process of claim 1, wherein the total length of the tubular reactor is 100 to 150 m.

18. The process of claim 1, wherein the diameter of the tubular reactor is 150 to 280 mm.

19. The process of claim 1, wherein the first reaction mixture, obtained by the feeding (a), has a temperature of 55 to 95° C.

20. The process of claim 1, wherein the second reaction mixture, obtained by the converting (b), has a temperature not exceeding 140° C.

* * * * *